US012773220B2

(12) United States Patent
Gao et al.

(10) Patent No.: US 12,773,220 B2
(45) Date of Patent: Oct. 27, 2026

(54) METHOD AND APPARATUS FOR VARIABLE SPEED OSTEOTOMY

(71) Applicant: KUANRUI INTELLIGENT TECHNOLOGY (SUZHOU) CO., LTD, Suzhou (CN)

(72) Inventors: Qiang Gao, Nanjing (CN); Yue Zhang, Nanjing (CN); Yinxi Lu, Nanjing (CN); Qiong Wu, Nanjing (CN)

(73) Assignee: KUANRUI INTELLIGENT TECHNOLOGY (SUZHOU) CO., LTD., Suzhou (CN)

( * ) Notice: Subject to any disclaimer, the term of this patent is extended or adjusted under 35 U.S.C. 154(b) by 481 days.

(21) Appl. No.: 18/261,843

(22) PCT Filed: Jan. 17, 2022

(86) PCT No.: PCT/CN2022/072308
§ 371 (c)(1),
(2) Date: Jul. 18, 2023

(87) PCT Pub. No.: WO2022/152292
PCT Pub. Date: Jul. 21, 2022

(65) Prior Publication Data

US 2024/0366233 A1 Nov. 7, 2024

(30) Foreign Application Priority Data

Jan. 18, 2021 (CN) ......................... 202110061351.3

(51) Int. Cl.
*A61B 17/14* (2006.01)
*A61B 17/00* (2006.01)
*A61B 17/16* (2006.01)

(52) U.S. Cl.
CPC ............ *A61B 17/14* (2013.01); *A61B 17/142* (2016.11); *A61B 17/1626* (2013.01);
(Continued)

(58) Field of Classification Search
CPC .. A61B 17/16–1628; A61B 17/14–149; A61B 17/17–1796; A61B 17/32–326
See application file for complete search history.

(56) References Cited

U.S. PATENT DOCUMENTS 6,665,948 B1 * 12/2003 Kozin .................... A61B 90/06 175/45
8,226,336 B2 * 7/2012 Brady ..................... B23B 35/00 408/1 R
(Continued)

FOREIGN PATENT DOCUMENTS

CN 103513094 A 1/2014
CN 103976772 A 8/2014
(Continued)

OTHER PUBLICATIONS

International Search Report for PCT/CN2022/072308, mailed on Mar. 30, 2022.
(Continued)

*Primary Examiner* — Matthew J Lawson
(74) *Attorney, Agent, or Firm* — Junhe Law Office P.C.; James J. Zhu

(57) ABSTRACT

A method and apparatus for variable speed osteotomy are provided. The method includes: controlling a bone saw to perform an osteotomy operation at a first speed in a first tissue; acquiring a power representation signal of the bone saw; processing the power representation signal to acquire a high frequency component and a low frequency component; performing, based on a predefined threshold, a denoising operation on the high frequency component to obtain a denoised high frequency component; reconstructing the denoised high frequency component and the low frequency component to obtain a denoised power representation signal; determining, based on the denoised power representation signal, whether the bone saw enters a second tissue which
(Continued)

has different properties from the first tissue; and when determined that the bone saw enters the second tissue, controlling the bone saw to perform an osteotomy operation at a second speed.

11 Claims, 6 Drawing Sheets

(52) U.S. Cl.
CPC ............... *A61B 2017/00017* (2013.01); *A61B 2017/00039* (2013.01); *A61B 2017/00398* (2013.01)

(56) References Cited

U.S. PATENT DOCUMENTS

| | | | | |
|---|---|---|---|---|
| 8,734,153 | B2 * | 5/2014 | Arzanpour | A61C 1/0007 433/131 |
| 10,195,007 | B2 * | 2/2019 | Ahmadi | A61C 1/055 |
| 11,517,327 | B2 * | 12/2022 | McGinley | A61B 17/1626 |
| 11,576,684 | B2 * | 2/2023 | McGinley | A61B 90/98 |
| 2005/0116673 | A1 | 6/2005 | Carl et al. | |
| 2005/0131415 | A1 * | 6/2005 | Hearn | B25B 23/147 606/80 |
| 2010/0143861 | A1 * | 6/2010 | Gharib | A61C 5/40 433/81 |
| 2014/0222003 | A1 | 8/2014 | Herndon et al. | |
| 2015/0342618 | A1 * | 12/2015 | Nguyen | A61B 17/1688 433/27 |
| 2016/0066972 | A1 * | 3/2016 | Corpa de la Fuente | A61B 17/8847 606/92 |
| 2016/0128704 | A1 * | 5/2016 | McGinley | A61B 17/17 606/86 R |
| 2019/0365346 | A1 * | 12/2019 | Elliot | A61B 6/505 |
| 2020/0014948 | A1 * | 1/2020 | Lai | H04N 19/436 |
| 2020/0054410 | A1 * | 2/2020 | Pfotenhauer | A61B 17/1626 |
| 2024/0016471 | A1 * | 1/2024 | Bourlion | A61B 8/0841 |
| 2024/0382224 | A1 * | 11/2024 | Vu | A61B 17/1626 |

FOREIGN PATENT DOCUMENTS

| | | | |
|---|---|---|---|
| CN | 204520865 | U | 8/2015 |
| CN | 108985179 | A | 12/2018 |
| CN | 112716559 | A | 4/2021 |

OTHER PUBLICATIONS

Search Report for the counterpart Chinese patent application 202280010590.9, mailed on May 26, 2026.

* cited by examiner

METHOD AND APPARATUS FOR VARIABLE SPEED OSTEOTOMY

TECHNICAL FIELD

The present application relates to the technical field of medical devices, and more specifically, to a method and apparatus for variable speed osteotomy for a surgical robot.

BACKGROUND OF THE INVENTION

In orthopedic clinics, osteotomy operations are relatively common. For example, in artificial joint replacement surgery, artificial biomaterials are used to replace diseased joints in the human body to restore the normal physiological function of the joints. In surgery, doctors need to perform individualized osteotomy to the patient's joint to match the artificial joint prosthesis. However, during the osteotomy operation, the bone saw needs to feed in different tissues (e.g., a muscle tissue, a compact bone and a cancellous bone, etc.), and the differences in density, hardness, and contact area with the bone saw of these different tissues will lead to variations in the contact force between the bone saw and the tissues, which results in the difficulty in controlling the speed of osteotomy.

Therefore, a safe and efficient method for controlling the speed of osteotomy is needed.

SUMMARY OF THE INVENTION

An objective of the present application is to provide a method for variable speed osteotomy, which can obtain an osteotomy state based on a power representation signal of a bone saw, so as to achieve variable speed osteotomy.

According to some aspects of the present application, a method for variable speed osteotomy is provided. The method comprises: controlling a bone saw to perform an osteotomy operation at a first speed in a first tissue; obtaining a power representation signal of the bone saw during the osteotomy operation; processing the power representation signal to obtain a high frequency component and a low frequency component of the power representation signal; performing, based on a predefined threshold, a denoising operation to the high frequency component to obtain a denoised high frequency component; reconstructing the denoised high frequency component and the low frequency component to obtain a denoised power representation signal; determining, based on the denoised power representation signal, whether the bone saw enters, from the first tissue, a second tissue having a different property from the first tissue; and controlling, when it is determined that the bone saw enters the second tissue from the first tissue, the bone saw to perform the osteotomy operation at a second speed in the second tissue.

According to some other aspects of the present application, an apparatus for variable speed osteotomy is provided. The apparatus comprises: a first control unit configured for controlling a bone saw to perform an osteotomy operation in a first tissue at a first speed; an obtaining unit configured for obtaining a power representation signal of the bone saw during the osteotomy operation; a processing unit configured for processing the power representation signal to obtain a high frequency component and a low frequency component of the power representation signal; a denoising unit configured for performing, based on a predefined threshold, denoising to the high frequency component to obtain a denoised high frequency component; a reconstruction unit configured for reconstructing the denoised high frequency component and the low frequency component to obtain a denoised power representation signal; a determination unit configured for determining, based on the denoised power representation signal, whether the bone saw enters, from the first tissue, a second tissue having a different property from the first tissue; and a second control unit configured for controlling the bone saw, when determined that the bone saw enters the second tissue from the first tissue, to perform an osteotomy operation at a second speed in the second tissue.

According to yet some other aspects of the present application, an electronic device is provided. The electronic device includes: a processor; and a storage apparatus for storing a computer program capable of running on the processor; wherein the computer program, when executed by the processor, causes the processor to perform the aforementioned method for variable speed osteotomy.

According to yet some other aspects of the present application, a non-volatile computer-readable storage medium is provided, wherein the non-volatile computer-readable storage medium has a computer program stored thereon, the computer program, when executed by a processor, performs the aforementioned method for variable speed osteotomy.

According to yet some other aspects of the present application, a method for detecting an osteotomy state is provided. The method includes: controlling a bone saw to perform an osteotomy operation; obtaining a power representation signal of the bone saw during the osteotomy operation; processing the power representation signal to obtain a high frequency component and a low frequency component of the power representation signal; performing, based on a predefined threshold, a denoising operation on the high frequency component to obtain a denoised high frequency component; reconstructing the denoised high frequency component and the low frequency component to obtain a denoised power representation signal; and determining an osteotomy state of the bone saw based on the denoised power representation signal.

The above is an overview of the application, and may be simplified, summarized and omitted in detail. Therefore, those skilled in the art should realize that this part is only illustrative, and is not intended to limit the scope of the application in any way. This summary section is neither intended to determine the key features or essential features of the claimed subject matter, nor is it intended to be used as an auxiliary means to determine the scope of the claimed subject matter.

BRIEF DESCRIPTION OF DRAWINGS

Through the following detailed description in conjunction with the accompanying drawings and the appended claims, those skilled in the art will more fully understand the above and other features of the content of this application. It can be understood that these drawings only depict several exemplary embodiments of the content of the present application, and should not be considered as limiting the scope of the content of the present application. By referring to the drawings, the content of this application will be explained more clearly and in detail.

DETAILED DESCRIPTION OF THE INVENTION

Figure 1:
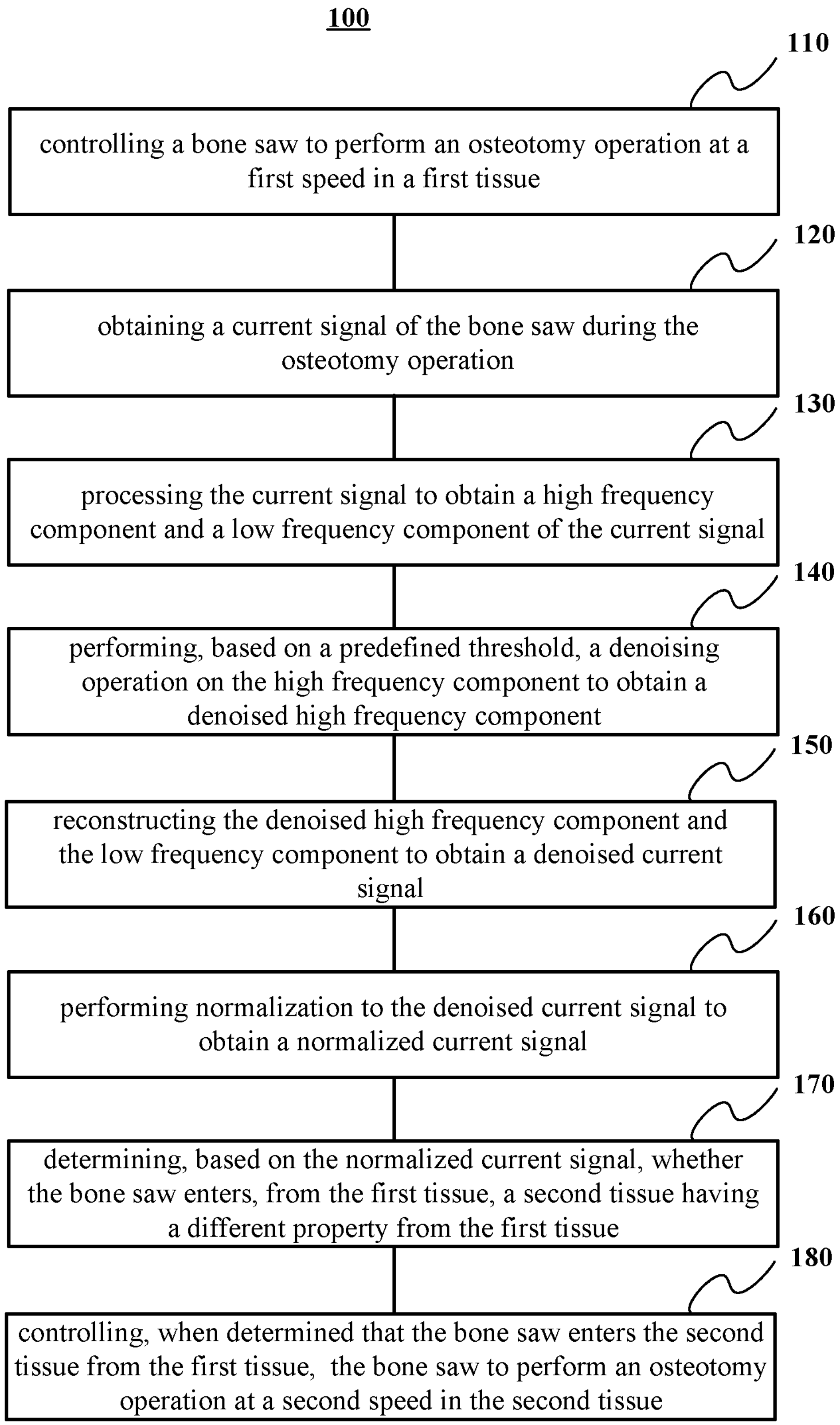
FIG. 1 illustrates a flowchart of a method for variable speed osteotomy according to some embodiments of the present application.

In the following detailed description, reference is made to the drawings constituting a part of the specification. In the drawings, unless the context dictates otherwise, similar symbols usually indicate similar components. The illustrative embodiments described in the detailed description, drawings, and claims are not meant to be limiting. Without departing from the spirit or scope of the subject matter of the present application, other implementation modes can be adopted and other changes can be made. It can be understood that various aspects of the content of the application generally described in the application and illustrated in the drawings can be configured, replaced, combined, and designed with various different configurations, and all of these clearly constitute part of the content of the application.

The inventors of the present application have found that when a bone saw is fed into tissues having different properties, the differences in the mechanical properties of the different tissues may lead to a difference in the magnitudes of the contact forces between the bone saw and the different tissues, and that the magnitude of the contact force between the bone saw and the tissue and the magnitude of the power of the bone saw motor are theoretically correlated. Therefore, detection of a signal representing the power magnitude of the bone saw motor can be used to identify the osteotomy state, for example, whether the bone saw enters from a muscle tissue into a bone tissue, or whether the bone saw enters from a cancellous bone into a compact bone, etc. However, it is difficult to accurately identify the osteotomy state using only the magnitude of the detected power representation signal of the bone saw motor, because in the process of detecting and obtaining the power representation signal, there are often signal abrupt changes in the obtained power representation signal. These signal abrupt changes may come from circuit filtering defects, external electromagnetic wave interferences, etc. These accidental abrupt changes seriously affect the determination of the real situation of the osteotomy state, resulting in the power representation signal being difficult to be directly used for identifying the osteotomy state.

Based on the above study of the prior art and the discovery of the problems therein, the inventors of the present application provides a variable speed osteotomy method in the present application. In the method, a power representation signal of a bone saw during an osteotomy operation is obtained and processed to obtain a high frequency component and a low frequency component of the power representation signal. Then, the high frequency component can be denoised based on a predefined threshold to obtain a denoised high frequency component; and then the denoised high frequency component and the low frequency component can be reconstructed to obtain a denoised power representation signal. In this way, signal abrupt changes introduced by various external factors in the power representation signal are eliminated or effectively suppressed to avoid affecting the determination and identification of the subsequent osteotomy state. Afterwards, it can be determined based on the denoised power representation signal whether the bone saw enters from a first tissue into a second tissue having a different property from the first tissue, such as entering from a muscle tissue into a bone tissue, or from a cancellous bone into a compact bone, etc. After determining that the bone saw enters the second tissue from the first tissue, a feed rate of the bone saw in the second tissue may then be adjusted as desired.

The inventors noticed that the noise signal in the power representation signal of the osteotomy motor is usually a high frequency signal. Accordingly, the power representation signal is decomposed into a high frequency component and a low frequency component in the variable speed osteotomy method of the present application, and only the high frequency component is denoised. This can filter out or reduce the noise while retaining or extracting the feature information in the power representation signal to the greatest extent, and thereby, it is beneficial to the identification of the osteotomy state.

The variable speed osteotomy method of the present application is described in detail below with reference to the accompanying drawings. FIG. 1 shows a flowchart of a variable speed osteotomy method 100 according to some embodiments of the present application, which specifically includes the following steps 110-180. It should be noted that, in the example of FIG. 1, the motor of the bone saw works in a constant voltage environment, and the power representation signal may be a current signal obtained by measuring current of the motor of the bone saw with a current measuring instrument. That is, in the description with reference to FIG. 1, the current signal and the power representation signal are interchangeable concepts. However, in some other embodiments, the power representation signal may be a power signal obtained by directly measuring the power of the motor of the bone saw with a power measuring instrument. In some yet other embodiments, the motor of the bone saw may also work in a constant current environment, and the power representation signal may be a voltage signal obtained by measuring the voltage of the motor of the bone saw with a voltage measuring instrument.

In step 110, the bone saw is controlled to perform osteotomy operation in a first tissue at a first speed.

Usually, the electric bone saw is configured with a saw blade, a mechanical reciprocating drive device and a motor. When used, the motor drives the mechanical reciprocating drive device to work, and the reciprocating drive device then drives the saw blade to carry out reciprocating motion for osteotomy, where the speed of osteotomy can be controlled by controlling the power of the motor. In some embodiments, in order to improve the stability of the osteotomy operation, the osteotomy operation can also be performed by the bone saw under control of a robot.

In an example, an osteotomy operation may be performed on a bone tissue (e.g., a knee bone) using a multi-degree-of-freedom robot. During the osteotomy operation, the skin and muscle may be cut open, and there exists a process where the bone saw enters the bone tissue from air and returns to air after completing the osteotomy operation. In this example, the air serves as the first tissue, and the bone saw is controlled to feed in the air at a first speed (e.g., a feed rate of 1 mm/s, a rotational speed of 10,000 r/min) to approach the sample bone. In other examples, there may be a situation where part of the muscle tissue, skin tissue, or cartilage tissue, etc. is not cut open, then the first tissue may also be the muscle tissue, skin tissue, or cartilage tissue, etc., and the corresponding first speed may be configured according to the actual situations, and is not limited in this application.

In step 120, a current signal of the bone saw is obtained during the osteotomy operation.

In some embodiments, the current signal may be obtained by sampling the motor current of the bone saw during the osteotomy operation at a preset sampling frequency or a preset sampling period. For example, the motor current of the bone saw is sampled at a sampling period of 30 ms. In some other examples, the sampling period may be 10 ms, 20 ms, 40 ms, 50 ms or other suitable time values.

Figure 2:
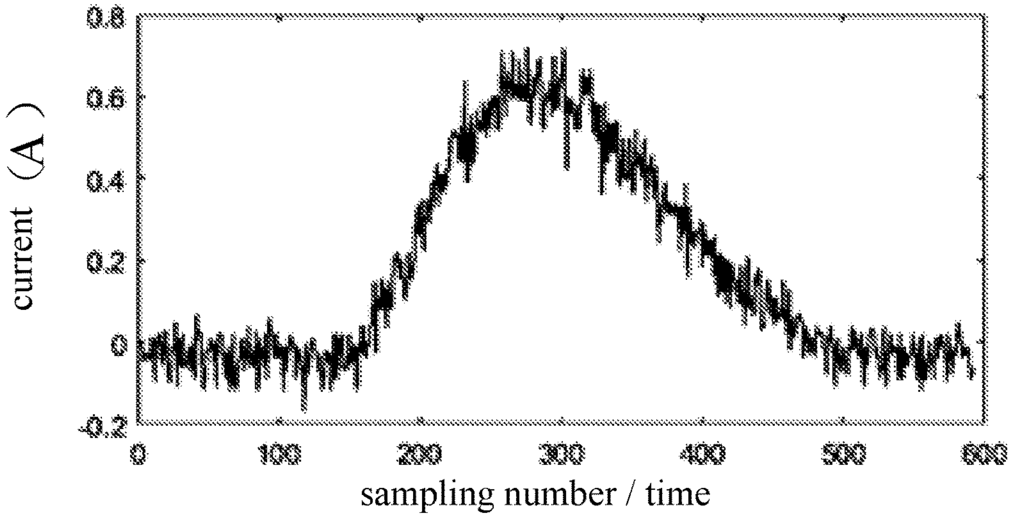
FIG. 2 illustrates a schematic diagram of a current signal obtained by sampling the motor current of a bone saw according to some embodiments of the present application.

Referring to FIG. 2, it illustrates a schematic diagram of a current signal obtained in an exemplary embodiment by sampling a motor current of a bone saw with a sampling period of 30 ms, wherein the horizontal axis indicates the sampling number (which corresponds roughly to the sampling time), and the vertical axis indicates the magnitude of the sampled current. As can be seen from FIG. 2, although the overall current signal shows a trend of changing along with changing of the bone saw operation state, the current signal contains relatively large random fluctuation noise in a local period. These noises may be caused by circuit filtering defects, external electromagnetic wave interference, or other factors. Therefore, the current signal must be processed with noise filtering before feature information of the current signal being extracted, and then accurate feature information can be extracted.

In step 130, the current signal is processed to obtain a high frequency component and a low frequency component of the current signal.

As mentioned above, noise signals in the current signal are usually caused by circuit filtering defects, external electromagnetic wave interference, and the like. These noises are more likely to affect the high frequency component of a current signal, so it is necessary to discretize the high frequency component and the low frequency component of the current signal, and then process the high frequency component to filter out or reduce the noise.

In some embodiments, the current signal is processed using wavelet filtering to obtain the high frequency component and the low frequency component of a current signal.

A wavelet can be described as a function, and a mathematical expression is used to describe the wavelet, i.e. it is a function $\psi(x)$ that satisfies the following Equation (1):

$$C_\omega = \int_{-\infty}^{+\infty} \frac{|\hat{\psi}(\omega)|^2}{|\omega|} d\omega < \infty \tag{1}$$

wherein, $\psi(x)$ is a mother wavelet function, $\hat{\psi}(\omega)$ is a fourier transform of the mother wavelet function $\psi(x)$, and $C_\omega$ is called the admissible constant. The basic requirement of a wavelet transform is to decompose the original signal or function into a series of wavelet functions, and then the wavelet functions are processed and reconstructed, where these wavelet functions are obtained from the mother wavelet function $\psi(x)$ by translational and scaling transforms. In an example, the wavelet function $\psi_{a,b}(x)$ (or wavelet basis function) can be expressed as in Equation (2) below:

$$\psi_{a,b}(x) = \frac{1}{\sqrt{|a|}} \psi\left(\frac{x-b}{a}\right) \tag{2}$$

where a represents the scale factor of the wavelet function $\psi_{a,b}(x)$ relative to the mother wavelet function $\psi(x)$. When a is larger than 1, the mother wavelet function $\psi(x)$ is expanded, and when a is smaller than 1, the mother wavelet function $\psi(x)$ is compressed, which is related to the frequency information in the transform domain. b represents the translation factor of the wavelet function $\psi_{a,b}(x)$ relative to the mother wavelet function $\psi(x)$, which represents the movement of the wavelet function in the signal, and is related to the time information in the transform domain. The frequency domain localization information of the original signal can be obtained by changing the value of a, and the time domain localization information of the signal can be obtained by changing the value of b.

Theoretically, we can use the continuous wavelet transform to process the current signal to obtain the high frequency component and the low frequency component of the current signal. Assuming that the current signal is represented by the objective function $f(x)$, the continuous wavelet transform of the current signal is defined in Equation (3) below:

$$w_f(a, b) = \frac{1}{\sqrt{|a|}} \int_{-\infty}^{+\infty} f(x) \psi\left(\frac{x-b}{a}\right) dx = \langle f(x), \psi_{a,b}(x) \rangle \tag{3}$$

wherein $w_f(a, b)$ is the wavelet coefficient. The corresponding inverse transformation of Equation (3) is defined in Equation (4) below:

$$f(x) = \frac{1}{C_\omega} \int_0^{+\infty} \int_{-\infty}^{+\infty} w_f(a, b) \psi_{a,b}(x) \frac{1}{a^2} dx da \tag{4}$$

However, since a large number of calculations have to be performed by computers, which are only suitable for processing discretized digital data, therefore, the continuous wavelet transform cannot be computed in their integral form, but need to be discretized. The discretized wavelet transform of the objective function $f(x)$ representing the current signal is defined in Equation (5) below:

$$w_f(2^j, 2^j k) = 2^{-\frac{j}{2}} \int_{-\infty}^{+\infty} f(x) \psi(2^{-j} x - k) dx \tag{5}$$

wherein $w_f(2^j, 2^j k)$ is the discretized wavelet coefficient, $2^j$ denotes the discretization of the scale factor a, $2^j k$ denotes the discretization of the translation factor b, both j and k are integers, and $$2^{-\frac{j}{2}} \Psi(2^j x - k)$$

denotes the discretized wavelet function.

The corresponding inverse transformation of Equation (5) is defined in Equation (6) below:

$$f(x) = C\sum_{j=-\infty}^{+\infty}\sum_{k=-\infty}^{+\infty} w_f(2^j, 2^j k)\psi_{(2^j,2^j k)}(x) \quad (6)$$

where C is a constant independent of the signal.

In an example, the current signal is discretized using wavelet decomposition to obtain a high frequency component and a low frequency component of the current signal. For example, a low-pass filter and a high-pass filter are constructed using a wavelet function (e.g., a db3 wavelet) with the scale factor having a base of 2, wherein the low-pass filter and the high-pass filter may be represented as matrices. Then, the wavelet coefficients of the current signal are subjected to an inner-product operation with the high-pass filter and the low-pass filter, respectively, to obtain coefficients for the high frequency portion and the low frequency portion of the current signal. Among them, the low frequency portion is the approximation portion of the current signal, and the high frequency portion is the detailed portion of the current signal. Although the high frequency portion contains most of the noise, the low frequency portion still also contain possible noise information. Therefore, instead of further processing the high frequency portion, the low frequency portion is further decomposed to obtain a second order high frequency portion and a second order low frequency portion of the low frequency portion. Moreover, it is also possible to continue with a third layer decomposition of the second order low frequency portion and so forth. It is to be noted that both too many and too few decomposition layers may be unfavorable to the subsequent denoising process, because too many decomposition layers will reduce the extracting effect of the intrinsic change rules and trends of the current signal, and too few decomposition layers will not be able to effectively separate the approximation portion and the detailed portion of the current signal. In different embodiments, a suitable number of decomposition layers may be selected according to actual needs. For example, the number of layers of wavelet decomposition may be determined based on comprehensive consideration of the actual trend of change of the current signal and its theoretical change regularity, and the present application does not limit the specific number of the layers of decomposition.

Figure 3:
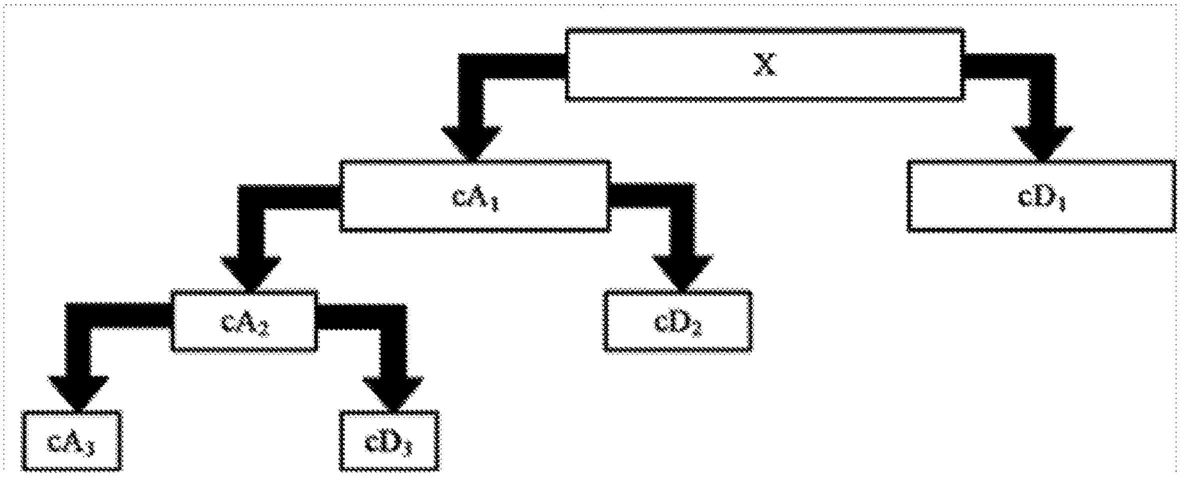
FIG. 3 illustrates a schematic diagram of a 3-layer discretization of the current signal according to some embodiments of the present application.

In an example, as shown in FIG. 3, a wavelet decomposition process is performed using the db3 wavelet function to discretize the current signal X to obtain a first order low frequency portion $cA_1$ and a first order high frequency portion $cD_1$; then the first order low frequency portion $cA_1$ is discretized to obtain a second order low frequency portion $cA_2$ and a second order high frequency portion $cD_2$; and then the second order low frequency portion $cA_2$ is discretized to obtain a third order low frequency portion $cA_3$ and a third order high frequency portion $cD_3$. In other words, a three-layer decomposition of the current signal X is performed. In this example, the first order high frequency portion $cD_1$, the second order high frequency portion $cD_2$, and the third order high frequency portion $cD_3$ constitute the high frequency component of the current signal; and the third order low frequency portion $cA_3$ after the 3-layer decomposition constitutes the low frequency component of the current signal. After the wavelet decomposition is completed, coefficients of the high frequency and low frequency portions of each order can be obtained, and subsequently, by processing the coefficients of the high frequency portions of each order, the wavelet reconstruction of the signal is carried out, such that the purpose of eliminating or reducing the noise can be achieved. In some other examples, the current signal X may also be decomposed into other numbers of layers, e.g., 1 layer, 2 layers, 4 layers, 5 layers, and the like. In some other examples, a wavelet decomposition of the current signal X may also be performed using haar, bior, coif, sym, or other wavelet basis.

In step 140, the high frequency component is denoised based on a predefined threshold to obtain a denoised high frequency component.

In some embodiments, the predefined threshold may be determined based on a maximum value of noise in the current signal, for example, the predefined threshold may be equal to or greater than the maximum value of noise. Generally, the maximum value of noise may be estimated with the following Equation (7):

$$T = \sigma\sqrt{2\log_e N} \quad (7)$$

wherein T denotes the maximum value of noise, and in the case where the predefined threshold value is equal to the maximum value of noise, T also denotes the predefined threshold value; σ denotes the standard deviation of the noise; and N denotes the sampling duration of the motor current of the bone saw, which may be determined based on the predefined sampling frequency stated above. Specifically, corresponding to the example in FIG. 3, the standard deviation of the noise σ may be determined based on the coefficient of the first order high frequency portion $cD_1$ obtained after discretization of the current signal X, and N is the sampling duration of the current signal X, e.g. 30 ms.

In some embodiments, the high frequency component of the current signal may be denoised using a global thresholding method. It should be noted that the denoising process of the decomposed current signal using the global thresholding method is performed only for the high frequency component and not for the low frequency component.

In some embodiments, a hard global thresholding method may be used to denoise the high frequency component of the current signal. Specifically, a coefficient of the high frequency component of the current signal is set to zero if the absolute value of the coefficient of the high frequency component of the current signal is below a threshold, and the coefficient remains unchanged if above the threshold. In an example, the hard global thresholding method is represented by the following Equation (8):

$$W_{new} = \begin{cases} W, & |W| \geq T \\ 0, & |W| < T \end{cases} \quad (8)$$

wherein $W_{new}$ denotes a coefficient of the high frequency component of the processed current signal; W denotes a coefficient of the high frequency component of the original current signal, such as a coefficient of the first order high frequency portion $cD_1$, a coefficient of the second order high frequency portion $cD_2$, and a coefficient of the third order high frequency portion $cD_3$ of FIG. 3; and T denotes the predefined threshold.

In other embodiments, the high frequency component of the current signal may also be denoised using a soft global thresholding method. Specifically, a coefficient of the high frequency component of the current signal is set to zero if the absolute value of the coefficient of the high frequency component of the current signal is below a threshold, and the coefficient is reassigned a value if it is above the threshold. In an example, the soft global thresholding method is represented by the following Equation (9):

$$W_{new} = \begin{cases} \text{sign}(W)(|W| - T), & |W| \geq T \\ 0, & |W| < T \end{cases} \tag{9}$$

Similar to Equation (8), $W_{new}$ denotes the coefficient of the high frequency component of the processed current signal, and W denotes the coefficient of the high frequency component of the original current signal; T denotes the predefined threshold; and sign(W) is a sign function, which can be expressed by the following Equation (10):

$$\text{sign}(W) = \begin{cases} 1, & W > 0 \\ 0, & W = 0 \\ -1, & W < 0 \end{cases} \tag{10}$$

Figure 4:
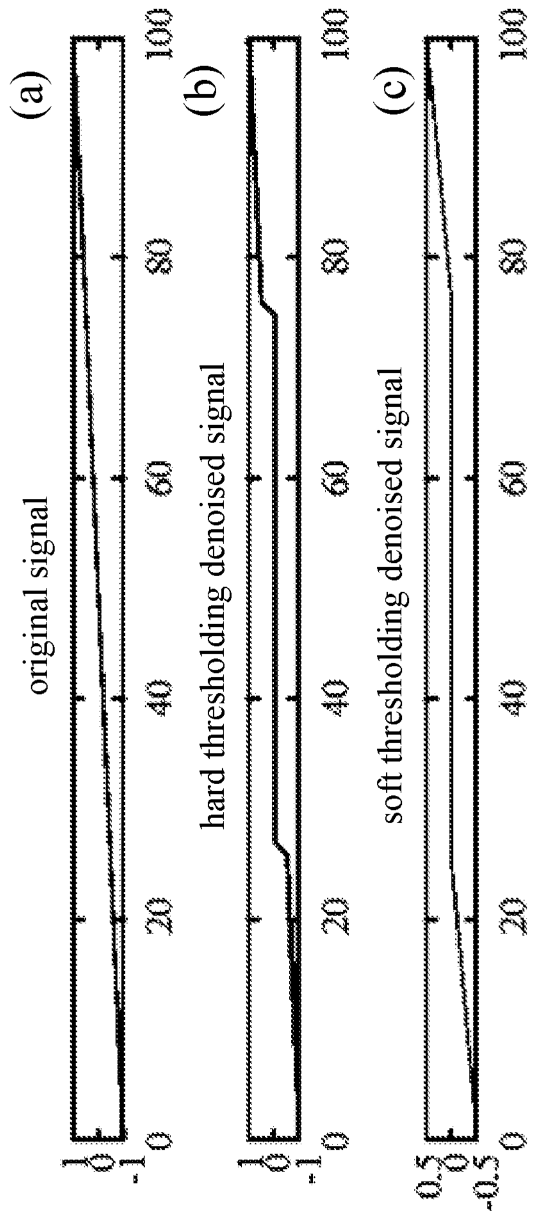
FIG. 4(*a*), FIG. 4(*b*), and FIG. 4(*c*) illustrate schematic diagrams of the original signal, the signal after hard thresholding, and the signal after soft thresholding, respectively, according to some embodiments of the present application.

Reference is made to FIGS. 4 (*a*), (*b*) and (*c*), which illustrate a comparison of the results of denoising the same signal by the hard global thresholding method and the soft global thresholding method, respectively. Therein, FIG. 4(*a*) represents the original signal, and for illustration purposes, in this example, the value of the function $f(x)=x/50-1$ in the interval [0,100] is taken as the original signal, and the predefined threshold is set to 0.5. FIG. 4(*b*) represents the signal after denoising the original signal by the hard global thresholding method; and FIG. 4(*c*) represents the signal after denoising the original signal by the soft global thresholding method. It can be seen that, after the hard thresholding, the signal curve is discontinuous at the threshold point; while after the soft thresholding, there are constant deviations between the processed curve and the original curve, where these deviations will affect reconstruction accuracy. Therefore, although both the hard thresholding and the soft thresholding can perform the denoising process of the high frequency component of the current signal, in order to obtain a higher accuracy of the reconstructed signal, the present application preferably uses a hard thresholding method to carry out the denoising process.

In step 150, the denoised high frequency component and the low frequency component are reconstructed to obtain the denoised current signal.

In some embodiments, the reconstruction of the current signal can be performed using the inverse transformation of the wavelet decomposition method in the preceding step 130, except that at this point, the first order high frequency portion $cD_1$, the second order high frequency portion $cD_2$, and the third order high frequency portion $cD_3$ of the original current signal have already been denoised by the global thresholding method, that is, some of the coefficients have already been set to zero or reassigned values. In an example, coefficients of the denoised high frequency component and the low frequency component may be subjected to an inner product operation with the conjugate matrices of the high-pass filter and the low-pass filter, respectively, and summed to obtain the denoised current signal.

Figure 5:
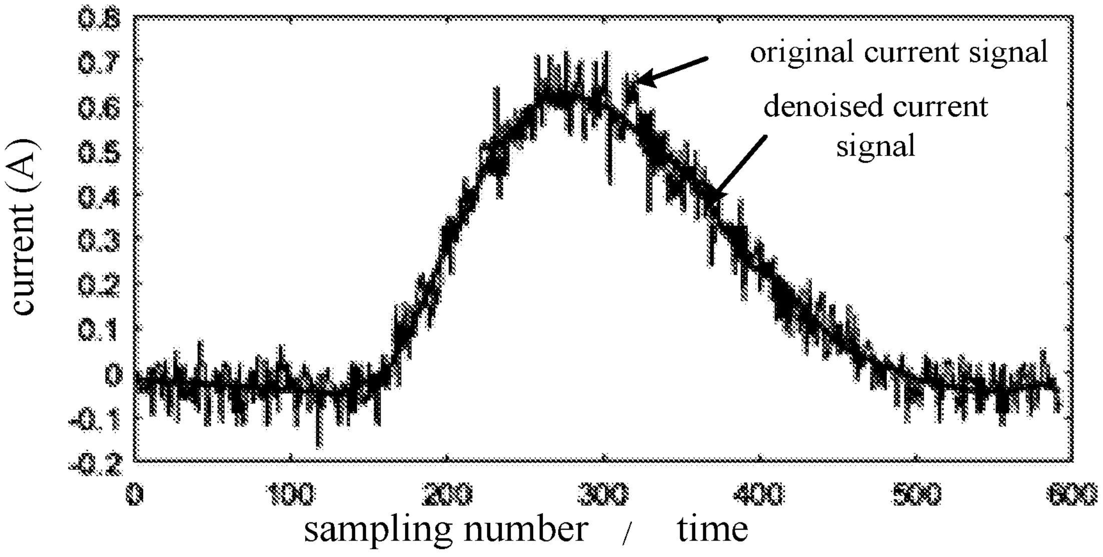
FIG. 5 illustrates a schematic diagram of the original current signal and the denoised current signal according to some embodiments of the present application.

Reference is made to FIG. 5, which illustrates a comparison graph comparing the curves of the denoised current signal obtained by reconstructing the denoised high frequency component and the low frequency component and the original current signal. It can be seen that the curve of the denoised current signal becomes smooth and does not change the morphology of the original signal, which can truly reflect the feature information of the original current signal.

In step 160, the denoised current signal is normalized to obtain a normalized current signal.

In the osteotomy operation, different osteotomy parameters will have a large effect on the current of the bone saw motor. Even under the same conditions and with the osteotomy parameters fixed, since there exists bone quality difference in individual patients (e.g., a difference in bone hardness), it can lead to different current signals of the osteotomy motor during the osteotomy process. Therefore, it is difficult to apply a fixed critical current threshold to recognize different stages of the entire osteotomy process. To avoid such differences, the denoised current signal can be normalized.

In some embodiments, it is chosen to normalize the denoised current signal using an arc cotangent function transformation, such that the normalized current signal as a whole falls between [−1, 1], forming a statistical coordinate distribution. The expression of the arc cotangent function can be expressed by the following Equation (11):

$$y = \frac{2 \cdot \tan^{-1}(x)}{\pi} \tag{11}$$

wherein x denotes the value of the current signal after denoising before transformation; and y denotes the value of the current signal after normalization.

Figure 6:
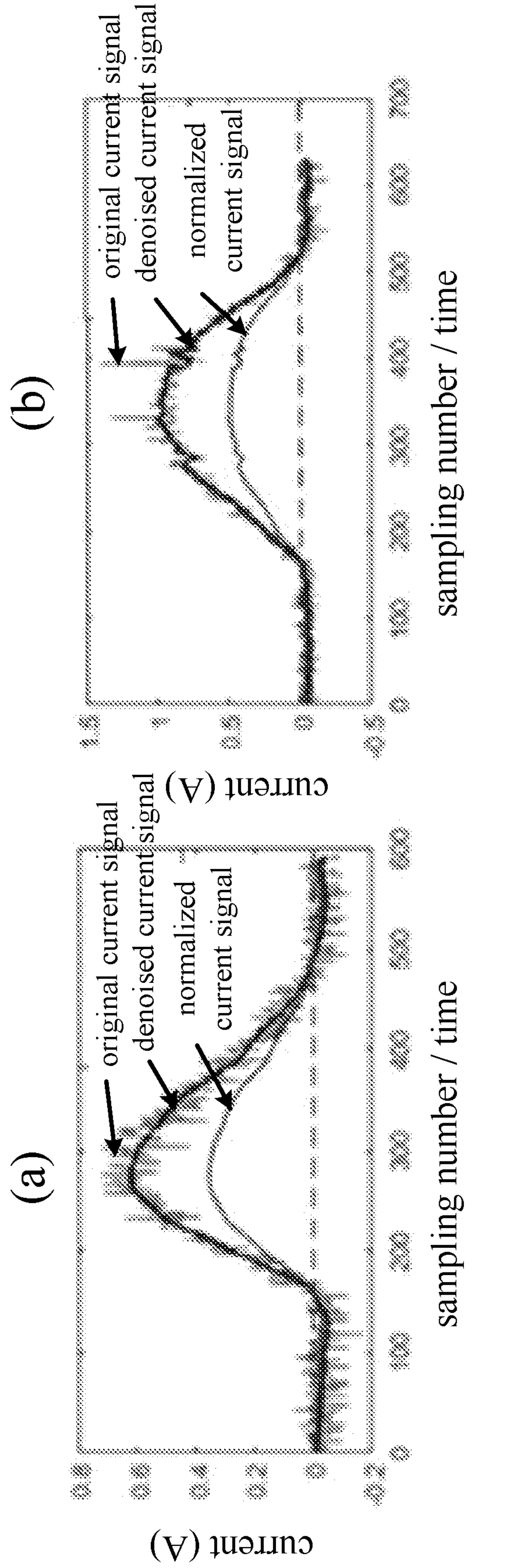
FIG. 6(*a*) and FIG. 6(*b*) illustrate schematic diagrams of the original current signal, the denoised current signal, and the normalized current signal under different osteotomy parameters according to some embodiments of the present application.

Reference is made to FIGS. 6(*a*) and (*b*), wherein FIG. 6(*a*) illustrates the original current signal, the denoised current signal and the normalized current signal under the osteotomy parameter with a feed rate of 1 mm/s and a rotational speed of 10,000 r/min; and FIG. 6(*b*) illustrates the original current signal, the denoised current signal and the normalized current signal under the osteotomy parameter with a feed rate of 1.5 mm/s and a rotational speed of 8000 r/min. It can be seen that the normalized current signal under different osteotomy parameters can fall within [−1, 1].

In some other embodiments, the denoised current signal may also be normalized using other normalization methods, such as linear normalization, standard deviation normalization, logarithmic normalization, and the like.

In step 170, based on the normalized current signal, it is determined whether the bone saw enters from a first tissue into a second tissue having a different property from the first tissue.

Since the second tissue has a different property from the first tissue, for example, a different hardness, a different density, a different contact area with the bone saw, and the like, a change in the motor current of the bone saw may occur when the bone saw enters the second tissue from the first tissue. The aforementioned change may be presented by an abrupt change in the current signal in the normalized current signal. Accordingly, a critical power representation threshold (in this embodiment, referred to as a critical current threshold) may be determined based on the difference in the properties of the first tissue and the second tissue (e.g., including the difference in hardness, the difference in density, the difference in contact area with the bone saw, etc.); and then, it is determined whether or not a value of the normalized current signal exceeds the critical current threshold, so as to determine whether the bone saw enters from the first tissue into the second tissue.

Figure 7:
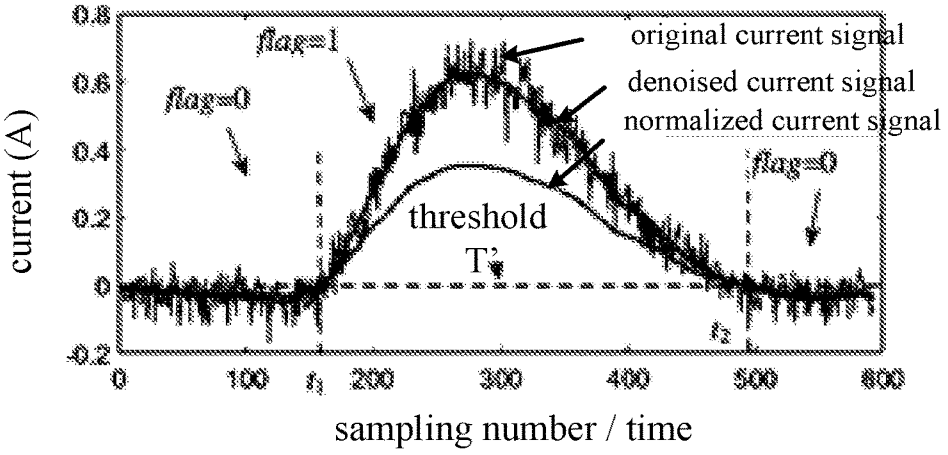
FIG. 7 illustrates a schematic diagram of determining an osteotomy state based on the normalized current signal according to some embodiments of the present application.

Referring to FIG. 7, it shows variation curves of the original current signal, the denoised current signal, and the normalized current signal during the process of the bone saw entering the sample bone from air to complete the osteotomy and re-entering the air in an example osteotomy operation. It can be appreciated that in the example, the first tissue is air and the second tissue is the sample bone. As can be seen from FIG. 7, the normalized current signal is below and close to the critical current threshold T' before the moment t1. In this example, before the moment t1, the motor of the bone saw is in an idle state in air and the output power is close to 0. Due to the presence of noise and burrs in the current, the normalized current signal may be located under 0 before the moment t1 (indicated by flag=0 on the left side in FIG. 7), i.e., the threshold value T' is 0 in this example. At the moment t1, the normalized current signal undergoes an abrupt change and starts to rise above the critical current threshold T', which means that the bone saw starts to enter the sample bone from the air to perform osteotomy, and the output power starts to increase. Between moments t1 and t2, it stays above the critical current threshold T', i.e., the bone saw performs osteotomy in the sample bone with a positive output power (indicated by flag=1 in FIG. 7). Then, at the moment of t2, there is another abrupt change and the normalized current signal starts to go under the critical current threshold T' and maintains under the critical current threshold T' after the moment t2, which means that the bone saw completes the osteotomy operation to the sample bone and returns from the sample bone to the air, and the motor of the bone saw is in an idle state in the air and the output power is close to 0 (indicated by flag=0 on the right side in FIG. 7). Thereby, based on analyzing whether the normalized current signal crosses the critical current threshold T', it can be determined whether the bone saw enters the sample bone from the air or whether it enters the air from the sample bone.

In the example of FIG. 7, it is illustrated with the first tissue being air and the second tissue being sample bone, and the critical current threshold of the normalized current signal is 0. In other examples, the first tissue may be a muscle tissue and the second tissue may be bone tissue, such that the osteotomy operation of the bone saw in both the muscle tissue and the bone tissue outputs a positive power, and the normalized current signal will always be above the point of value 0. Thereby, it is determined that the critical current threshold of the current signal will also be greater than 0. That is, based on the difference in the properties of the first tissue and the second tissue, the critical current threshold determined as the normalized current signal may be different in different application scenarios.

How the critical current threshold of the current signal is determined is one aspect of identifying changes in the state of the bone saw osteotomy operation. In some embodiments, a threshold current corresponding to a point of the abrupt change in the osteotomy state may be determined based on experimental statistics, theoretical calculations, and/or empirical values, so that a moment corresponding to the point of abrupt change in the osteotomy state may be determined by comparing the threshold current with the processed current signal.

In step 180, when it is determined that the bone saw enters the second tissue from the first tissue, the bone saw is controlled to perform the osteotomy operation at a second speed in the second tissue.

Continuing with FIG. 7 as an example, prior to the moment t1, the bone saw feeds in the air at a constant first speed, and at the moment t1, the bone saw is determined to enter the sample bone from the air. In order to achieve a safe and efficient osteotomy, the feeding speed of the bone saw can be smoothly increased at the moment t1, so that the bone saw's feeding speed in the sample bone changes to a second speed. Therein, the first speed and the second speed may be a preset constant speed or a preset changing speed profile, respectively.

It should be noted that the feeding speed of the bone saw usually has a positively correlated correspondence with the rotational speed of the bone saw motor, so the rotational speed of the bone saw motor can be changed by changing the current of the bone saw motor, thereby changing the feeding speed of the bone saw. For example, each increase of 10 mA current corresponds to an increase of 20 r/min on the original configured rotational speed of the bone saw motor. However, usually in view of the smoothness of the speed adjustment, a rotational speed increase is preferably configured to be no more than 100 r/min in each time interval of 100 ms. In other embodiments, the increase of the rotational speed of the bone saw motor may also be realized by increasing the output power of the bone saw motor.

It is noted that in the embodiment of FIG. 1, after obtaining the denoised current signal, step 160 is also performed, i.e. the denoised current signal is normalized to obtain the normalized current signal. However, in some other embodiments, step 160 may not be performed, i.e., it is directly determined based on the denoised current signal whether the bone saw enters from the first tissue into the second tissue having a different property. Accordingly, the subsequent determination process is determined based on whether the value of the denoised current signal crosses the critical current threshold. Also, in different implementations with and without the normalization process, the critical current threshold determined based on the property difference between first tissue and the second tissue may be different.

In the abovementioned variable speed osteotomy method, by decomposing the bone saw current signal into a high frequency component and a low frequency component and de-noising only the high frequency component, it is possible to maximally retain or extract the feature information in the current signal while filtering out or reducing the noise, which is conducive to identifying the osteotomy state. By recognizing the osteotomy state, variable speed osteotomy can be realized. For example, when the osteotomy has not reached the bone, the bone saw feeds in a constant speed, and when the osteotomy reaches the bone, the feeding speed smoothly increases, thereby realizing a relatively safe and efficient osteotomy.

It is also noted that in the embodiment of FIG. 1, the method of the present application for variable speed osteotomy is illustrated with the power representation signal as a current signal. However, it could be understood that the description in conjunction with FIG. 1 is equally applicable to the case where the power representation signal is a power signal or a voltage signal, including operations such as obtaining, discretizing, reconstructing, denoising, and normalizing the power signal or the voltage signal, and accordingly determining critical power representation threshold based on the property difference between the first tissue and the second tissue may be a critical power threshold and a critical voltage threshold.

In addition, embodiments of the present application provide methods for detecting an osteotomy state. The method includes: controlling a bone saw to perform osteotomy operation; obtaining a power representation signal of the bone saw during the osteotomy operation; processing the power representation signal to obtain a high frequency component and a low frequency component of the power representation signal; denoising the high frequency component based on a predefined threshold value to obtain a denoised high frequency component; reconstructing the denoised high frequency component and the low frequency component to obtain a denoised power representation signal; and determining an osteotomy state of the bone saw based on the denoised power representation signal. Based on the method, it is possible to automatically determine information such as whether the bone saw has entered the target tissue for osteotomy operation or whether it is functioning properly (e.g., whether it is jammed, etc.), so that based on such state information it is possible to adjust parameters of the osteotomy operation (e.g., to adjust the osteotomy speed, etc.) or to send an alarm to the operator of the bone saw, etc. Specific details regarding the method for detecting the osteotomy status can refer to the contents of the method for variable speed osteotomy described above in combination with FIGS. 1-7, and will not be repeated herein.

Figure 8:
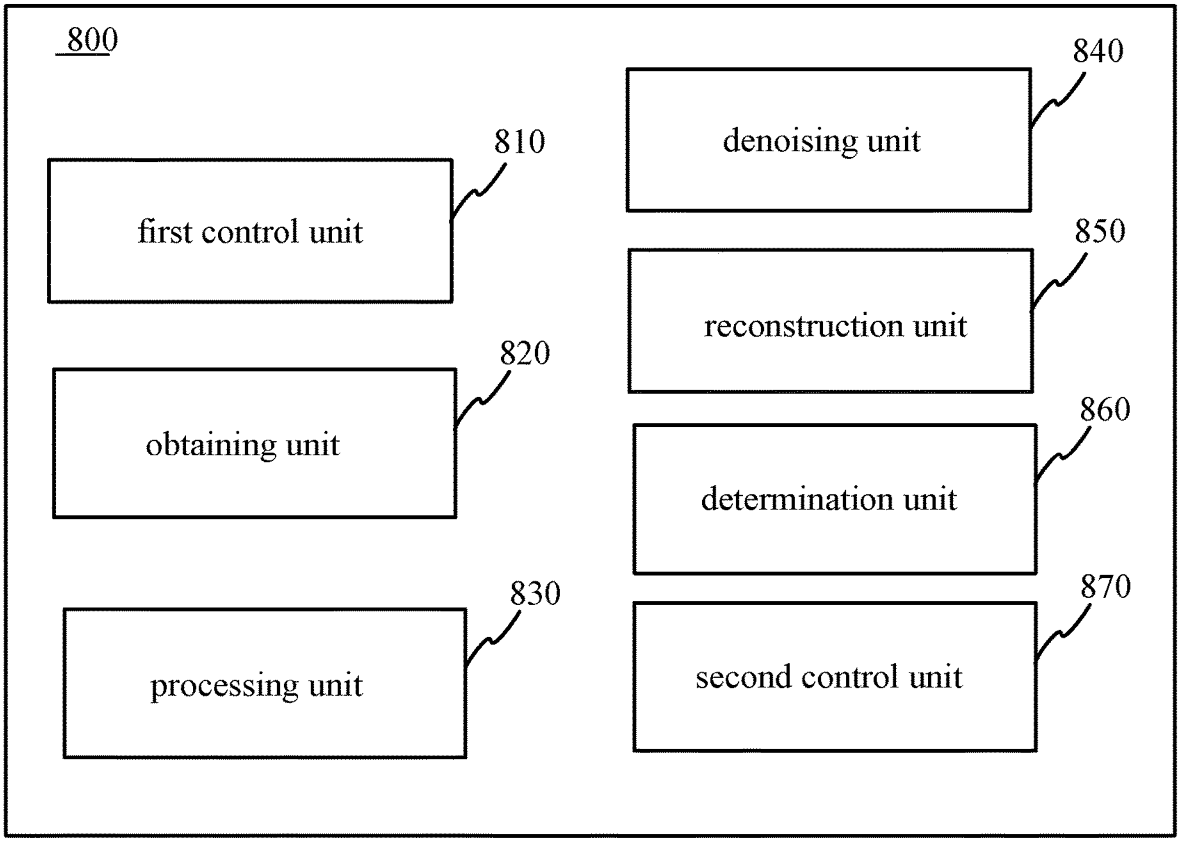
FIG. 8 illustrates a block diagram of an apparatus for variable speed osteotomy according to some embodiments of the present application.

In addition, embodiments of the present application provide a device 800 for variable speed osteotomy. As shown in FIG. 8, the device 800 for variable speed osteotomy includes a first control unit 810, an obtaining unit 820, a processing unit 830, a denoising unit 840, a reconstruction unit 850, a determination unit 860, and a second control unit 870. The first control unit 810 is used for controlling the bone saw to perform osteotomy operation at a first speed in a first tissue; the obtaining unit 820 is used for obtaining a power representation signal of the bone saw during the osteotomy operation; the processing unit 830 is used for processing the power representation signal to obtain a high frequency component and a low frequency component of the power representation signal; the denoising unit 840 is used for denoising the high frequency component based on a predefined threshold value to obtain a denoised high frequency component; and the reconstruction unit 850 is used for reconstructing the denoised high frequency component and the low frequency component to obtain a denoised power representation signal; the determination unit 860 is used for determining, based on the denoised power representation signal, whether the bone saw enters from a first tissue into a second tissue having a different property from the first tissue; the second control unit 870 is used for, when determined that the bone saw enters the second tissue from the first tissue, controlling the bone saw to perform an osteotomy operation at a second speed in the second tissue. A detailed introduction of the device 800 can refer to the above description of the corresponding method in combination with FIGS. 1 to 7, and will not be repeated here.

In some embodiments, the apparatus for variable speed osteotomy may be implemented as one or more application specific integrated circuits (ASIC), digital signal processors (DSP), digital signal processing devices (DSPD), programmable logic devices (PLD), field programmable gate arrays (FPGA), controllers, micro-controllers, microprocessors or other electronic devices. Moreover, the apparatus described above are only illustrative, and the division of units is merely based on logic functions, and the division manner may be implemented in other ways in practice. For example, multiple units or components can be combined or integrated within another system, or some features can be ignored or can be non-executed. Also, the illustrated or discussed coupling or direct coupling or communicative coupling between each other can be implemented through some interfaces, and indirect coupling or communicative connection between devices or units can be electronic or in other manners. The units shown as discrete components may be or may not be separate physically, and the components shown as units may be or may not be physical units, i.e. they can be arranged in a single position or distributed to multiple network units. A portion of all of the units can be selected to implement the embodiments of the present application according to actual needs.

In some other embodiments, the device for variable speed osteotomy may also be realized in the form of a software functional unit. When the functional units are implemented as software functional units and sold or used as separate products, they can be stored in a computer readable storage medium, and can be performed by a computing device. Based on such understanding, the technical solution or a contribution to the prior art of the present application or a part or all of the technical solution can be embodied in a software product which can be stored in a storage medium and include instructions executable by a computing device (e.g. a personal computer, a mobile terminal, a server or a network device, etc.) to perform a portion or all of the steps of the method according to the embodiments of the present application.

Embodiments of the present application also provides an electronic device, which includes a processor and a storage device. The storage device is configured to store a computer program that can run on the processor. When the computer program is executed by the processor, the processor is caused to execute the method for variable speed osteotomy in the foregoing embodiments. In some embodiments, the electronic device may be a mobile terminal, a personal computer, a tablet computer, a server, etc. mounted on or coupled to a bone saw.

Embodiments of the present application also provide a non-transitory computer-readable storage medium, the non-transitory computer-readable storage medium stores a computer program, and when the computer program is executed by a processor, the method for variable speed osteotomy is performed. In some embodiments, the non-transitory computer-readable storage medium may be a flash memory, a read only memory (ROM), an electrically programmable ROM, an electrically erasable and programmable ROM, register, hard disk, removable disk, CD-ROM, or any other form of non-transitory computer-readable storage medium known in the art.

Other variations to the disclosed embodiments can be understood and implemented by those skilled in the art by studying the specification, drawings and accompanying drawing. In the claims, wording “comprise” does not exclude other elements and steps, and wordings “a” and “one” do not exclude plural. In the practical application of the present application, an element may perform the functions of a plurality of technical features cited in the claims. Any reference markers in the claims should not be construed as limiting the scope.

The invention claimed is:

1. A method for variable speed osteotomy, comprising:

controlling a bone saw to perform an osteotomy operation at a first speed in a first tissue;

obtaining a power representation signal of the bone saw during the osteotomy operation;

processing the power representation signal to obtain a high frequency component and a low frequency component of the power representation signal;

performing, based on a predefined threshold, a denoising operation on the high frequency component to obtain a denoised high frequency component;

reconstructing the denoised high frequency component and the low frequency component to obtain a denoised power representation signal;

normalizing the denoised power representation signal to obtain a normalized power representation signal, wherein the normalization uses an arc cotangent function;

determining, based on the normalized power representation signal, whether the bone saw enters, from the first tissue, a second tissue having a different property from the first tissue; and controlling, when it is determined that the bone saw enters the second tissue from the first tissue, the bone saw to perform the osteotomy operation at a second speed in the second tissue.

2. The method of claim 1, wherein the power representation signal is obtained by sampling, at a predetermined sampling frequency, a signal representing a motor power of the bone saw during the osteotomy operation.

3. The method of claim 2, wherein processing the power representation signal to obtain a high frequency component and a low frequency component of the power representation signal comprises:

discretizing the power representation signal using wavelet decomposition to obtain the high frequency component and the low frequency component of the power representation signal.

4. The method of claim 3, wherein discretizing the power representation signal using wavelet decomposition comprises:

discretizing the power representation signal using a wavelet function to obtain a first order low frequency portion and a first order high frequency portion of the power representation signal;

discretizing the first order low frequency portion using the wavelet function to obtain a second order low frequency portion and a second order high frequency portion of the power representation signal; and discretizing the second order low frequency portion using the wavelet function to obtain a third order low frequency portion and a third order high frequency portion of the power representation signal, wherein the high frequency component of the power representation signal comprises the first order high frequency portion, the second order high frequency portion, and the third order high frequency portion; and the low frequency component of the power representation signal comprises the third order low frequency portion.

5. The method of claim 4, wherein the wavelet function is a db3 wavelet.

6. The method of claim 4, wherein the predefined threshold is determined based on a maximum value of noise in the power representation signal.

7. The method of claim 6, wherein the maximum value of noise is determined based on a sampling duration of a signal representing a motor power of the bone saw and a coefficient of the first order high frequency portion of the power representation signal.

8. The method of claim 4, wherein performing, based on a predefined threshold, a denoising operation on the high frequency component comprises:

comparing each of coefficients of the first order high frequency portion, the second order high frequency portion and the third order high frequency portion with the predefined threshold;

setting the coefficient to zero when the coefficient is greater than the predefined threshold; and remaining the coefficient unchanged when the coefficient is less than the predefined threshold.

9. The method of claim 1, wherein determining, based on the normalized power representation signal, whether the bone saw enters, from the first tissue, a second tissue having a different property from the first tissue comprises:

determining, based on a property difference between the first tissue and the second tissue, a critical power representation threshold; and determining, when a value of the normalized power representation signal exceeds the critical power representation threshold, that the bone saw enters the second tissue from the first tissue.

10. The method of claim 1, wherein the power representation signal is a power signal, a current signal or a voltage signal.

11. A method for detecting an osteotomy state, comprising:

controlling a bone saw to perform an osteotomy operation;

obtaining a power representation signal of the bone saw during the osteotomy operation;

processing the power representation signal to obtain a high frequency component and a low frequency component of the power representation signal;

performing, based on a predefined threshold, a denoising operation on the high frequency component to obtain a denoised high frequency component;

reconstructing the denoised high frequency component and the low frequency component to obtain a denoised power representation signal;

normalizing the denoised power representation signal to obtain a normalized power representation signal, wherein the normalization uses an arc cotangent function; and determining an osteotomy state of the bone saw based on the normalized power representation signal.

* * * * *